United States Patent
Lee (10) Patent No.: US 9,649,162 B2
(45) Date of Patent: *May 16, 2017

(54) STEREOTACTIC POSITIONING GUIDE APPARATUS

(71) Applicant: Choon Kee Lee, Denver, CO (US)

(72) Inventor: Choon Kee Lee, Denver, CO (US)

(*) Notice: Subject to any disclaimer, the term of this patent is extended or adjusted under 35 U.S.C. 154(b) by 382 days.

This patent is subject to a terminal disclaimer.

(21) Appl. No.: 14/311,338

(22) Filed: Jun. 22, 2014

(65) Prior Publication Data

US 2015/0366619 A1 Dec. 24, 2015

(51) Int. Cl.
| | | |
|---|---|---|
| A61B 19/00 | (2006.01) |
| A61B 8/00 | (2006.01) |
| A61B 90/11 | (2016.01) |
| A61B 34/20 | (2016.01) |
| A61B 17/34 | (2006.01) |

(52) U.S. Cl.
CPC .......... *A61B 19/201* (2013.01); *A61B 8/4272* (2013.01); *A61B 90/11* (2016.02); *A61B 2017/3413* (2013.01); *A61B 2034/2063* (2016.02)

(58) Field of Classification Search
CPC ... A61B 8/0841; A61B 8/4218; A61B 8/4272; A61B 8/4483; A61B 17/3403; A61B 2017/3413
See application file for complete search history.

(56) References Cited

U.S. PATENT DOCUMENTS

| | | | |
|---|---|---|---|
| 4,290,309 A * | 9/1981 | Charlebois | A61B 8/00 73/621 |
| 5,623,931 A | 4/1997 | Wung | |
| 5,941,889 A | 8/1999 | Cermak | |
| 6,203,499 B1 | 3/2001 | Imling | |
| 6,475,152 B1 | 11/2002 | Kelly, Jr. | |
| 6,485,426 B2 | 11/2002 | Sandhu | |
| 7,691,066 B2 | 4/2010 | Kosaku | |
| 7,846,103 B2 | 12/2010 | Cannon, Jr. | |
| 7,976,469 B2 | 7/2011 | Bonde | |
| 8,057,487 B2 | 11/2011 | Chu | |
| 8,073,529 B2 | 12/2011 | Cermak | |
| 8,118,743 B2 | 2/2012 | Park | |
| 8,216,149 B2 | 7/2012 | Oonuki | |
| 8,241,301 B2 | 8/2012 | Zhang | |
| 8,257,264 B2 | 9/2012 | Park | |
| 8,496,593 B2 | 7/2013 | Park | |
| 8,521,257 B2 | 8/2013 | Whitcomb | |
| 8,574,160 B2 | 11/2013 | Gorzitze | |
| 8,706,186 B2 | 4/2014 | Fichtinger | |
| 2002/0058872 A1 | 5/2002 | Steininger | |

(Continued)

*Primary Examiner* — Matthew F Desanto (57) ABSTRACT

The present invention presents an apparatus and methods to stereotactically guide insertion of invasive tubular devices to a tissue target of a living body. The apparatus comprises a positioning guide control assembly and a positioning guide assembly that is reversibly coupled with and operated by the positioning guide control assembly, and rotationally adjustable and lockable. The positioning guide control assembly releasably houses a ultrasound transducer head to visualize and aim at the tissue target and adjusts an insertion angle of an invasive tubular device placed in the positioning guide assembly.

5 Claims, 6 Drawing Sheets

(56) References Cited

U.S. PATENT DOCUMENTS

| | | | |
|---|---|---|---|
| 2007/0073155 A1* | 3/2007 | Park | A61B 8/0833 |
| | | | 600/461 |
| 2011/0313293 A1 | 12/2011 | Lindekugel | |
| 2012/0059260 A1 | 3/2012 | Robinson | |
| 2012/0259221 A1* | 10/2012 | Sheldon | A61B 8/462 |
| | | | 600/439 |
| 2013/0066192 A1 | 3/2013 | Sarvestani | |
| 2013/0197355 A1 | 8/2013 | Lee | |
| 2013/0225984 A1 | 8/2013 | Cheng | |

\* cited by examiner

STEREOTACTIC POSITIONING GUIDE APPARATUS

TECHNICAL FIELD

The present invention relates generally to the field of positioning guidance of insertion of invasive devices in a living body for medical purposes. More specifically, the present invention provides an apparatus and methods to assist introduction of tubular devices into a tissue using ultrasound.

BACKGROUND OF THE INVENTION

An invasive tubular device can be guided under ultrasonographic visualization by an apparatus that numerically measures an insertion angle and a length of the invasive tubular device to reach a tissue target. Insertion angle of an invasive device can also be adjusted to various positions of an ultrasound transducer in relation to a center of the tissue target. The apparatus comprises a positioning guide for an invasive tubular device through which the invasive tubular device passes toward a tissue target and a positioning guide controller which adjusts angulation of the positioning guide by using ultrasonographic visual information or by calculated numerical information of a set of insertion angle and depth of the invasive tubular device to reach the tissue target. The positioning guide is configured to be coupled with the positioning guide controller in a way to separate the positioning guide, before inserting the invasive tubular device toward the tissue target, from the positioning guide controller following localization and angulation of the positioning guide. It would be technically advantageous for a majority of applications to have a free-standing positioning guide that would verify a correct positioning of the positioning guide before inserting invasive tubular devices by additional imaging modalities such as computerized tomogram or by repeating ultrasonogram. The free-standing positioning guide reversibly attached to a skin overlying the tissue target allows a few invasive tubular devices to be used interchangeably through the same positioning guide toward the same tissue target. For example, placement of a large vascular catheter in a blood vessel usually requires a probing needle, a guidewire that uses Seldinger technique to reach a target site, a dilator to widen a tissue leading up to a vascular wall for inserting a vascular catheter and a vascular catheter. Attachment of the free-standing positioning guide to the skin overlying the target frees an operator to use both hands for a series of procedures for manipulating these devices, without a need to hold the ultrasound probe by one hand.

There are other applications of the positioning guide, however, which would best be accomplished by an apparatus of a positioning guide coupled with a positioning guide controller throughout manipulations of invasive devices. In-process visualization of insertion procedures of invasive devices would be required for small lesions, lesions located near vital structures or lesions that move during invasive procedures by physiologic bodily function such as breathing, heartbeat or pulsating blood vessels to increase accuracy of the insertion and to reduce chances of potential complications of the procedure. An invasive device placed in the positioning guide can be visualized and monitored by the positioning guide controller which houses an ultrasound probe and holds the positioning guide it controls for insertion angle and depth. Multiple samplings from a few individual sites in a single lesion can be expedited by a coupled apparatus as all interested sites are visualized by a positioning guide controller in an ultrasonographic field and the positioning guide controller holding a positioning guide can select preferred sites for a series of sequential invasive procedures. One crucial advantage of using the coupled configuration of the apparatus over a free-standing positioning guide comes from a need to abort or change an invasive procedure after the procedure was initiated. There would be several reasons to abort or change invasive procedures even after an invasive device was inserted into a tissue, including an unexpected heterogeneity in consistency of the tissue that forces changes in an insertion path, a wrong insertion path that leads the invasive device to an area off a tissue target or an incidental damage to vital structures such as blood vessels. In these circumstances, a free-standing positioning guide once deployed to a skin region by a positioning guide controller will be wasted. In contrast, a positioning guide yet attached to and controlled by a positioning guide controller will be able to function until completion of an intended procedure.

SUMMARY OF THE INVENTION

The present invention provides an apparatus that assists insertion of invasive tubular devices to tissue with ultrasonographically visualized targeting approaches to a tissue target. The invention provides a means to rotationally adjust insertion angle of invasive devices to reach the tissue target, which can be monitored in an ultrasonographic field. The apparatus comprises a positioning guide control assembly and a positioning guide assembly which is reversibly attached to and operated by the positioning guide control assembly. The positioning guide control assembly releasably houses a ultrasound transducer head, coordinates adjustment of insertion angles of invasive devices with linear alignment between a point of the transducer head and the tissue target in an ultrasonographic field.

In one embodiment, the positioning guide assembly is provided in one or a plurality of configurations, including a cross configuration which comprises an upright tubular positioning guide and a pair of transverse cylinders irreversibly attached at a right angle to each opposite side of a lower portion of the outer wall of the tubular positioning guide, respectively. One transverse cylinder serves for rotation of the tubular positioning guide and the other transverse cylinder provides the tubular positioning guide with axial stability. Each transverse cylinder is slidably and rotatably housed in a tubular cylinder holder that is attached to a base plate located below said transverse cylinder.

In one embodiment, a cylinder holder for the rotation cylinder of the tubular positioning guide has a horizontal slot for a length to accommodate a part of a lock and release lever which snaps in and out of said horizontal slot. In between of an outer circumferential wall of the rotation cylinder and the inner wall of the rotation cylinder holder, a thin nonslip tubular elastomer is provided, encasing the outer wall of said rotation cylinder. The horizontal slot of the rotation cylinder holder is reversibly and circumferentially expandable to a degree upon engagement with the lock and release lever, which widens an inner tubular space of said rotation cylinder holder. Widening of the inner tubular space allows friction-less rotation of both the elastomer and rotation cylinder inside said rotation cylinder holder. Disengagement of the lock and release lever shrinks the circumference of said tubular space, which then holds fast both the tubular elastomer and rotation cylinder together. The rotation cylinder is fastened by friction generated by the circumferentially squeezed tubular elastomer encasing said rotation cylinder. A transverse cylinder for axial stability slides in a tubular space of a stabilizer cylinder holder and axially stabilizes the tubular positioning guide on rotation. A mid portion of the base plate is configured to provide an open space through which an invasive device passes from the tubular positioning guide to a tissue target.

In one embodiment, the base plate of the positioning guide assembly below the rotation cylinder holder has a flat male piece protruded in parallel with the longitudinal axis of the rotation cylinder holder from a lateral edge of said base plate. The male piece is configured to be dovetailed and reversibly insertable to a female slot of a half blind cutout under a bottom plate of the positioning guide control assembly to form a reversible flat lap joint that anchors the positioning guide assembly to the positioning guide control assembly. The male piece is vertically aligned with the lock and release lever disposed atop the rotation cylinder holder.

In one embodiment, the positioning guide assembly is configured to reversibly be anchored to the positioning guide control assembly by both insertion of the male piece to the female slot and insertion of the lock and release lever into a slot provided on an anterior upper panel of the positioning guide control assembly. Insertion of said lock and release lever into said slot is coincided with engagement of said lever with the horizontal slot of the rotation cylinder holder, which results in widening of the inner tubular space of said rotation cylinder holder. Retracting said lock and release lever from said slot of the positioning guide control assembly disengages said lever from the horizontal slot of the rotation cylinder holder, which allows the rotation cylinder holder to fasten the rotation cylinder. Following the retraction of the lock and release lever, the positioning guide assembly stays attached to the positioning guide control assembly by the flat lap joint between the male piece and the female slot. The lock and release lever can be reinserted to the anterior upper panel slot of the positioning guide control assembly, if necessary, for an invasive tubular device placed in the tubular positioning guide to be redirected.

In one embodiment, the positioning guide control assembly is provided in one or a plurality of configurations including a modular configuration which comprises a transducer housing enclosure, a positioning controller assembly, a position alignment assembly and a power and electronic control assembly. The transducer housing enclosure is provided in an open box configuration with its top and bottom portions open to allow a proximal portion of the transducer to slip in and out of said enclosure through the top portion and to allow a face portion of the transducer to contact an upper part of the position alignment assembly via a solid gel panel. The transducer housing enclosure is configured to hold fast the proximal portion of the transducer in a manner to align longitudinal and horizontal axes of the transducer in parallel with longitudinal and horizontal axes of said transducer housing enclosure, respectively. The horizontal axis of the transducer is used as a reference axis to calibrate angular displacement of the tubular positioning guide and the longitudinal axis of the transducer is used as a reference axis for the rotation cylinder to align a longitudinal axis of the tubular positioning guide with said longitudinal axis of the transducer.

In one embodiment, the positioning controller assembly is provided in one or a plurality of configurations including a rectangular box configuration which encloses a worm drive arrangement, a part of an electromagnetic pointing device of the position alignment assembly and the power and electronic control assembly. The worm drive comprises a longitudinal worm connected at a right angle to a worm gear with an output shaft of the worm gear protruding through a medial vertical sidewall of said rectangular box. A proximal end of the worm shaft is connected to a rotatable knob located outside an anterior sidewall. The output shaft of the worm gear is provided in one or a plurality of configurations including a longitudinal bar having more than two internal angles on cross-section of said bar. The output shaft releasably is inserted in a horizontal slot of the rotation cylinder of the tubular positioning guide of the positioning guide assembly. The rotation cylinder is rotated by the output shaft of the worm gear by rotation of the rotatable knob that transmits worm rotation to the worm gear.

In one embodiment, a rotary potentiometer is coaxially connected to the worm shaft, which translates rotational position changes of the worm into output voltage changes. The rotary potentiometer is configured to be linear in proportional difference between an actual output voltage and a calculated voltage based on position of a wiper that runs across a resistive track of the rotary potentiometer. The rotary potentiometer is electronically connected to the power and electronic control assembly that relays a range of variable output voltage from said rotary potentiometer based on rotational position changes of the worm shaft to the electromagnetic pointing device of the position alignment assembly.

In one embodiment, the position alignment assembly is provided in one or a plurality of electromechanical configurations, which comprises a substantially ultrasound-transparent flat rectangular box and the electromagnetic pointing device adjoining a central portion of one lateral sidewall of said flat rectangular box. The flat rectangular box is located below the face of the transducer, is filled with an ultrasound-transparent liquid which is electrically non-conductive. In one example, the electromagnetic pointing device comprises a galvanometer-type device that uses a range of variable voltage to radially move a linear movable pointer around a center of said device. The linear movable pointer is configured to protrude into a space in the flat rectangular box, to move inside said flat rectangular box from side to side and to block ultrasound transmission from a ultrasound transducer to a tissue target, which is visualized in a ultrasonographic view. A leakproof housing for the galvanometer-type device merges and seals off the flat rectangular box in one piece. A galvanometer-type device configuration comprises a U-shaped set of electromagnetic windings surrounding a central rotor.

In one embodiment, the power and electronic control assembly is provided in one or a plurality of configurations including a rectangular box configuration which has a segment digital display on a top portion. An integrated circuit board is located under and electronically connected to the segment digital display. A compartment for replaceable batteries is located below the integrated circuit board and connects batteries electrically with the integrated circuit board, the segment digital display, the rotary potentiometer and the electromagnetic pointing device. The power and electronic control assembly is located in an upper part of the positioning controller assembly and the segment digital display is configured to be visible through an upper panel of the positioning controller assembly. The segment digital display shows at least a set of digitized numerical information about angular displacement of the rotation cylinder of the positioning guide assembly connected to the worm gear and distance from a position of the linear movable pointer tangentially placed over the tissue target to said tissue target.

In another embodiment, the power and electronic control assembly is configured to control movements of the electromagnetic pointing devices upon a range of variable output voltage from the rotary potentiometer. In this configuration, rotation of the rotation cylinder of the positioning guide assembly by the rotatable knob of the worm drive arrangement translates into ultrasonographically visualizable movement of the linear movable pointer in parallel to the transducer face located above the flat rectangular box of the position alignment assembly. In a two-dimensional ultrasonographic view, the linear movable pointer is configured to produce a thin vertical blank shadow line, by blocking ultrasound transmission, which can be distinguished readily from surrounding tissue images. Rotations of said rotation cylinder are configured to match horizontal movements of said linear movable pointer in ways that a longitudinal axis of an invasive device at an insertion angle in the positioning guide assembly crosses a vertical blank shadow line at a center of a tissue target in the two-dimensional ultrasonographic view.

BRIEF DESCRIPTION OF THE DRAWINGS

FIG. 1-1 represents an example of a positioning guide assembly; 2 represents an ultrasound transducer head; 3 represents a solid gel panel; 4 represents a positioning guide control assembly; 5 represents a second solid gel panel; 6 represents a fully assembled apparatus with an ultrasound transducer in place.

FIG. 2A represents a positioning guide assembly with a lock and release lever engaged with a rotation cylinder holder; FIG. 2B represents a positioning guide assembly with a disengaged lock and release lever and a rotated tubular positioning guide.

FIG. 3A represents an external view; FIG. 3B shows individual compartments inside the positioning guide control assembly with a transducer housing enclosure removed for illustration.

FIG. 5A shows locking and unlocking of the lock and release lever of the positioning guide assembly; FIG. 5B depicts a reversible flat lap joint made by a male piece of the positioning guide assembly and a half blind cutout of a female slot of a bottom plate of the positioning guide control assembly; FIG. 5C illustrates an example of reversible joint formation by both the male piece and female slot.

FIG. 5A shows a three-quarter view of a fully assembled components; FIG. 5B highlights a worm drive arrangement; FIG. 5C shows a position alignment assembly; FIG. 5D shows individual components of a galvanometer-type position alignment assembly.

DETAILED DESCRIPTION OF THE DRAWINGS

As described below, the present invention provides a positioning guide apparatus visually and stereotactically aiming at a tissue target and methods of use. It is to be understood that the descriptions are solely for the purposes of illustrating the present invention, and should not be understood in any way as restrictive or limited. Embodiments of the present invention are preferably depicted with reference to FIGS. 1 to 6, however, such reference is not intended to limit the present invention in any manner. The drawings do not represent actual dimension of devices, but illustrate the principles of the present invention.

Figure 1:
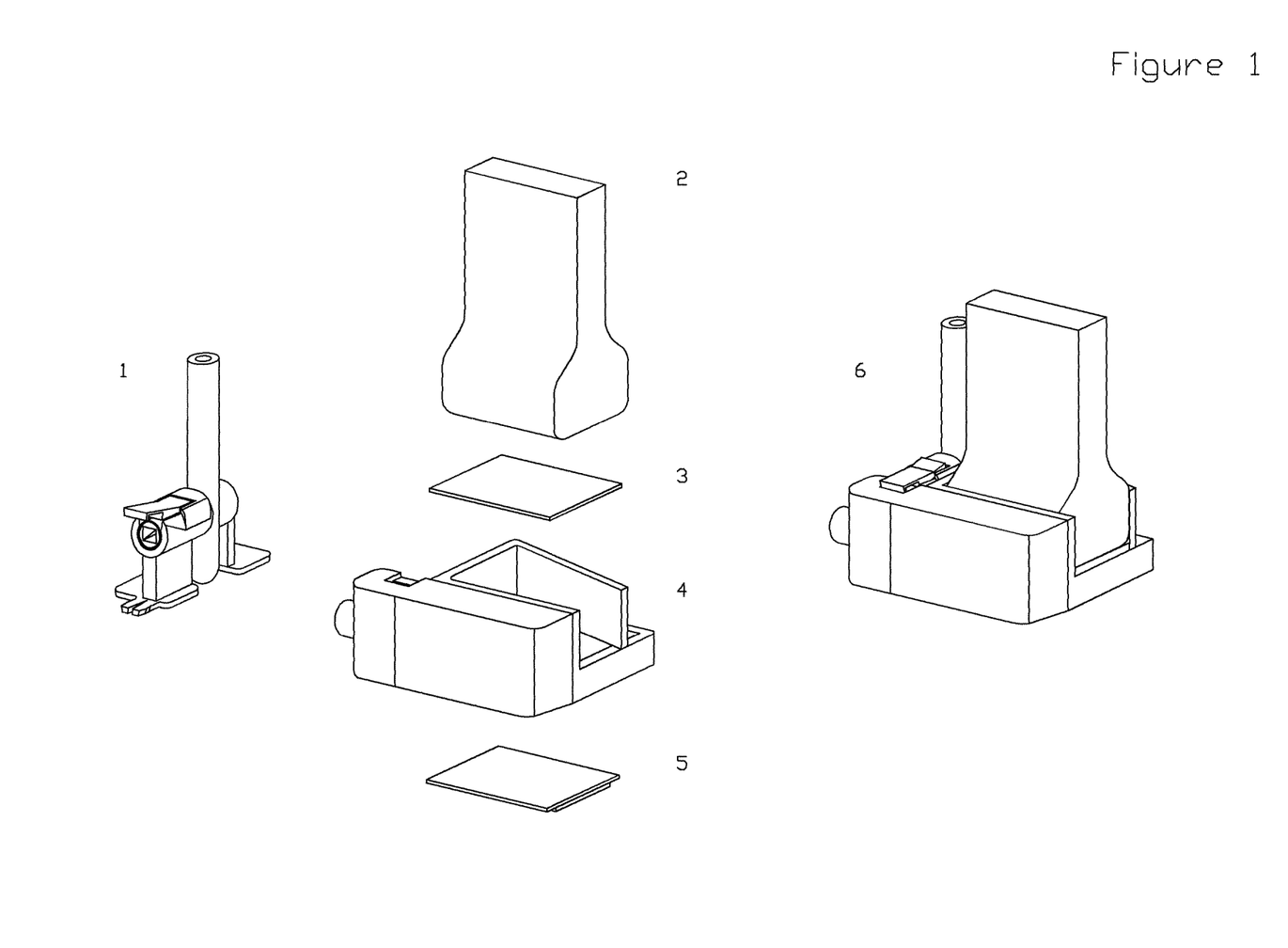
FIG. 1 shows a schematic illustration of an example of individual components of the apparatus of the present invention.

FIG. 1 shows a schematic example of individual components of the apparatus of the present invention. An example of a positioning guide assembly is shown in 1, which is coupleable with and operated by a positioning guide control assembly 4. An ultrasound transducer head 2 slides in and gets reversibly fastened to the positioning guide control assembly 4 and visualizes a tissue below through a couple of solid gel panels 3 and 5. An upper surface of the solid gel panel 3 placed in an open space provided in the positioning guide control assembly directly contacts a face of the ultrasound transducer head above and a lower surface of the other gel panel 5 placed in a most distal space of the said positioning guide control assembly contacts a skin below overlying the tissue. A lower surface of the solid gel panel 3 and an upper surface of the solid gel panel 5 contact a part of the positioning guide control assembly located in between of said solid gel panels 3 and 5. Solid gel panels improve transmission of ultrasound waves between the tissue and the ultrasound transducer. An example of a fully assembled apparatus is shown in 6. The positioning guide assembly 1 and the solid gel panels 3 and 5 are non-reusable.

Figure 2:
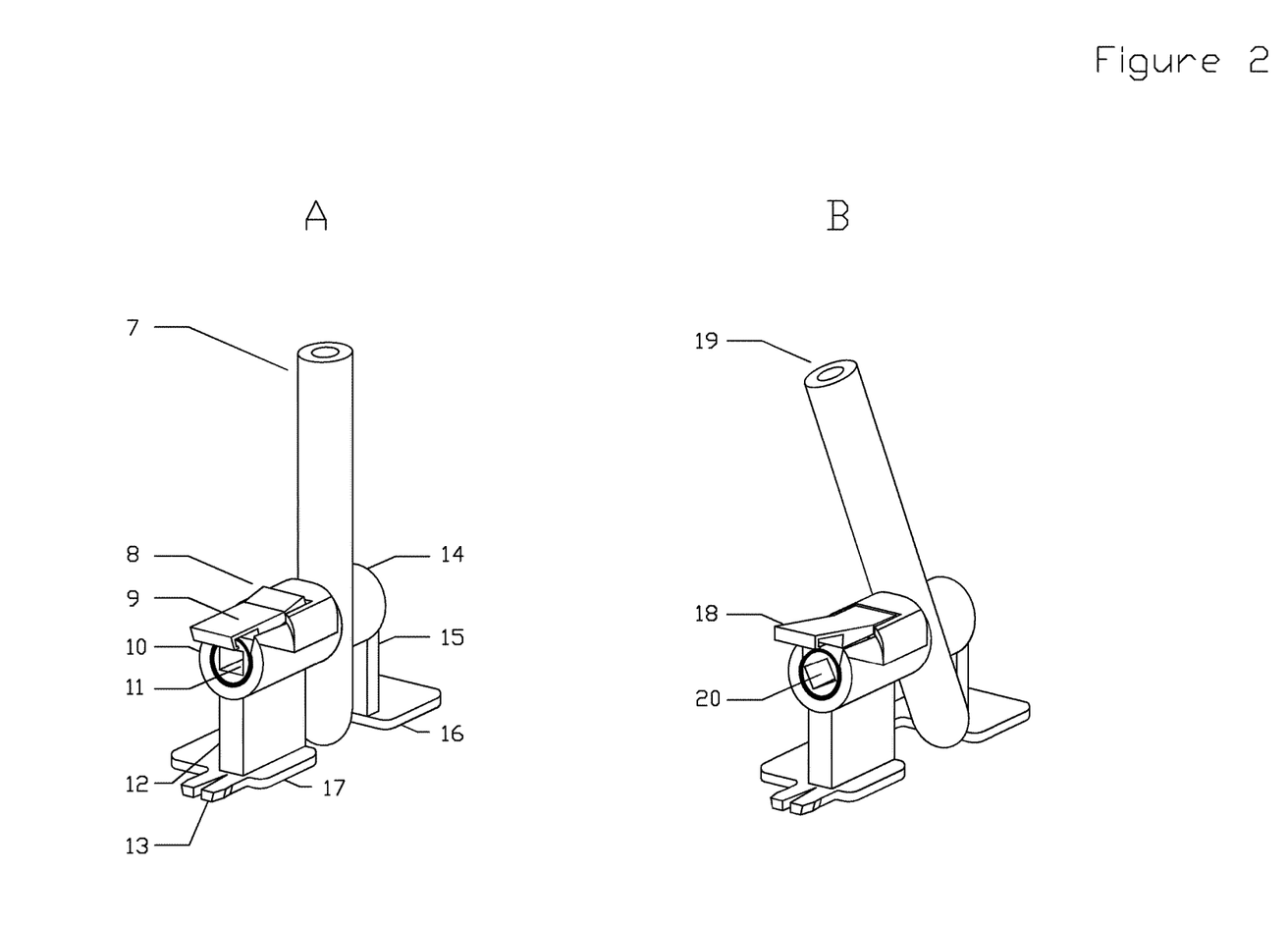
FIG. 2 shows a schematic example of the positioning guide assembly of the apparatus.

FIG. 2 shows a schematic example of the positioning guide assembly of the apparatus: FIG. 2A represents a positioning guide assembly in a fastened configuration to the positioning guide control assembly. In this particular configuration, the positioning guide assembly comprises a tubular positioning guide 7 in an upright position, a positioning guide rotation assembly 8 and a stabilizer cylinder holder 14. The positioning guide rotation assembly 8 comprises a lock and release lever 9 reversibly inserted in a rotation cylinder holder 10 and a rotation cylinder 11 encircled by said rotation cylinder holder 10. Both the rotation and stabilizer cylinder holders 10 and 14 are not attached to the tubular positioning guide 7 but irreversibly attached to an upper surface of a base plate. The rotation cylinder holder 10 is connected to a part 17 of the base plate via an attachment bar 12. The part 17 of the base plate has a flat male piece 13 protruded in parallel with the longitudinal axis of the rotation cylinder holder 10 from a lateral edge of said base plate. The male piece 13 is vertically aligned with the lock and release lever 9 disposed on top of the rotation cylinder holder 10. The stabilizer cylinder holder 14 is connected to a base plate 16 via an attachment bar 15. FIG. 2B represents a unlocked and rotated configuration of the positioning guide assembly with the lock and release lever 18 disengaged from the rotation cylinder holder. A tubular positioning guide 19 is rotated around a longitudinal axis 20 of the rotation cylinder and fixed at an angle.

Figure 3:
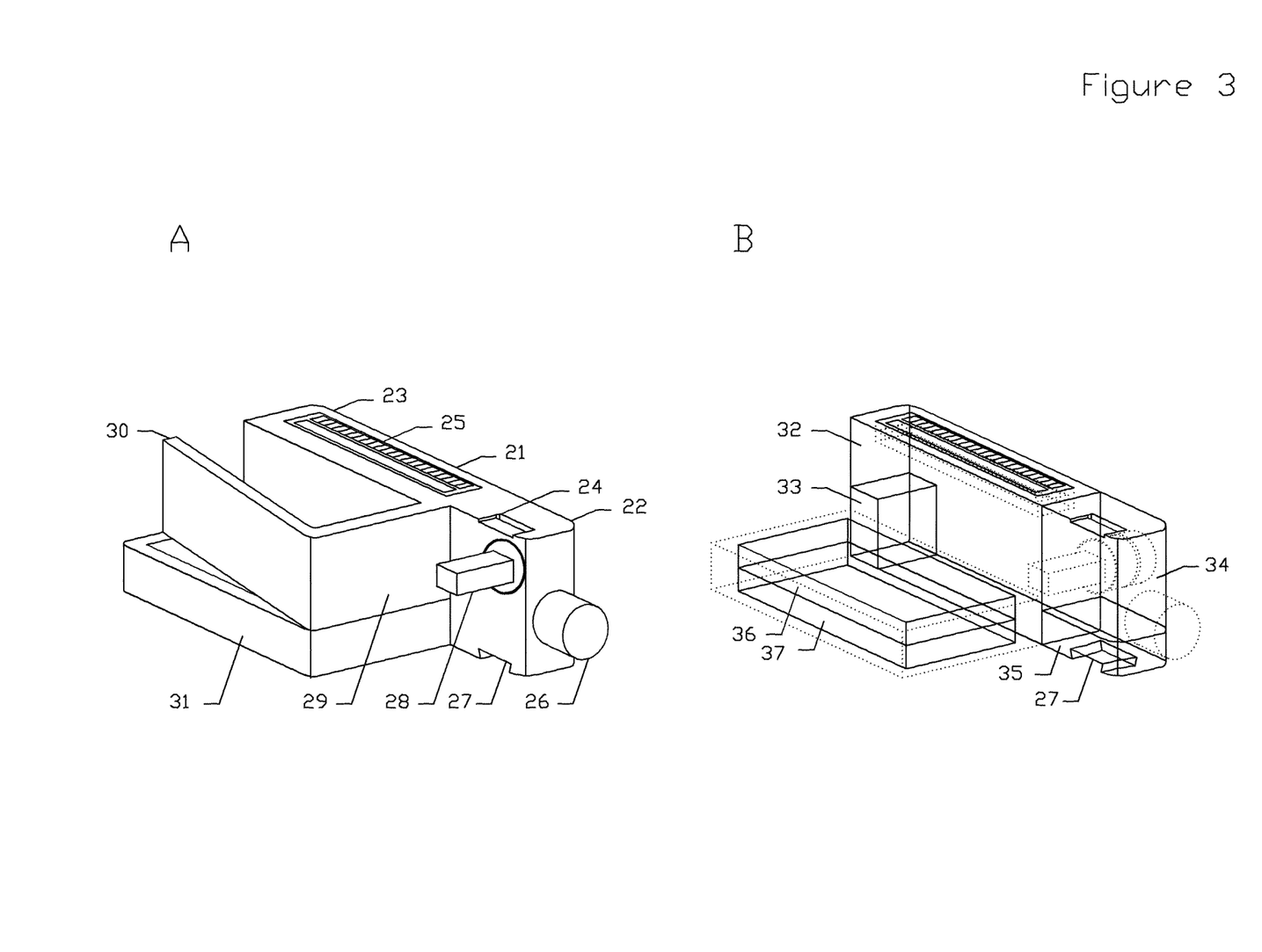
FIG. 3 shows a schematic example of the positioning guide control assembly.

FIG. 3 shows a schematic illustration of an example of the positioning guide control assembly. FIG. 3A represents an external three-quarter view which shows a positioning controller assembly 21 having a proximal end 22 and a distal end 23, a transducer housing enclosure 29 having a flexible free wall 30 and a position alignment assembly housing 31. The free wall 30 is flexible at a joint with an anterior sidewall of the transducer housing enclosure 29 in a manner that a transducer head is held fast inside the transducer housing enclosure 29. On an anterior upper surface of the positioning controller assembly 21, a slot 24 is provided vertically above an output shaft 28 of a worm drive arrangement, which fastens the lock and release lever 9 of the positioning guide assembly depicted in FIG. 2A to said positioning guide control assembly. The output shaft 28 releasably is inserted in a slot of the rotation cylinder 11 of FIG. 2A and rotates said rotation cylinder 11 as shown in FIG. 2. In a bottom plate of the proximal end 22, there is provided a female slot 27 open to a medial side of said proximal end. The female slot 27 is configured as a half blind cutout, which forms a reversible flat lap joint with the male piece 13 of FIG. 2A and is vertically aligned with the slot 24. A segment digital display 25 of a power and electronic control assembly is visible on the upper surface of said positioning controller assembly 21 along a longitudinal border. A rotatable knob 26 is connected to the worm drive arrangement inside said positioning controller assembly 21 through an anterior sidewall.

FIG. 3B shows individual compartments inside the positioning guide control assembly with a transducer housing enclosure removed for illustration. The positioning controller assembly 21 has a longitudinally rectangular compartment 32 which anteriorly adjoins a worm drive arrangement compartment 34 and a compartment 35 of a part of an electronic control assembly. The compartment 32 houses the power and electronic control assembly including a battery compartment 33, a part of the worm drive arrangement and a part of the positioning alignment assembly. A main part of the position alignment assembly is enclosed in a compartment 36 below which a compartment 37 releasably holds a solid gel panel. A lateral sidewall of both compartments 36 and 37 adjoins a medial sidewall of the positioning controller assembly compartment 32 at a right angle.

Figure 4:
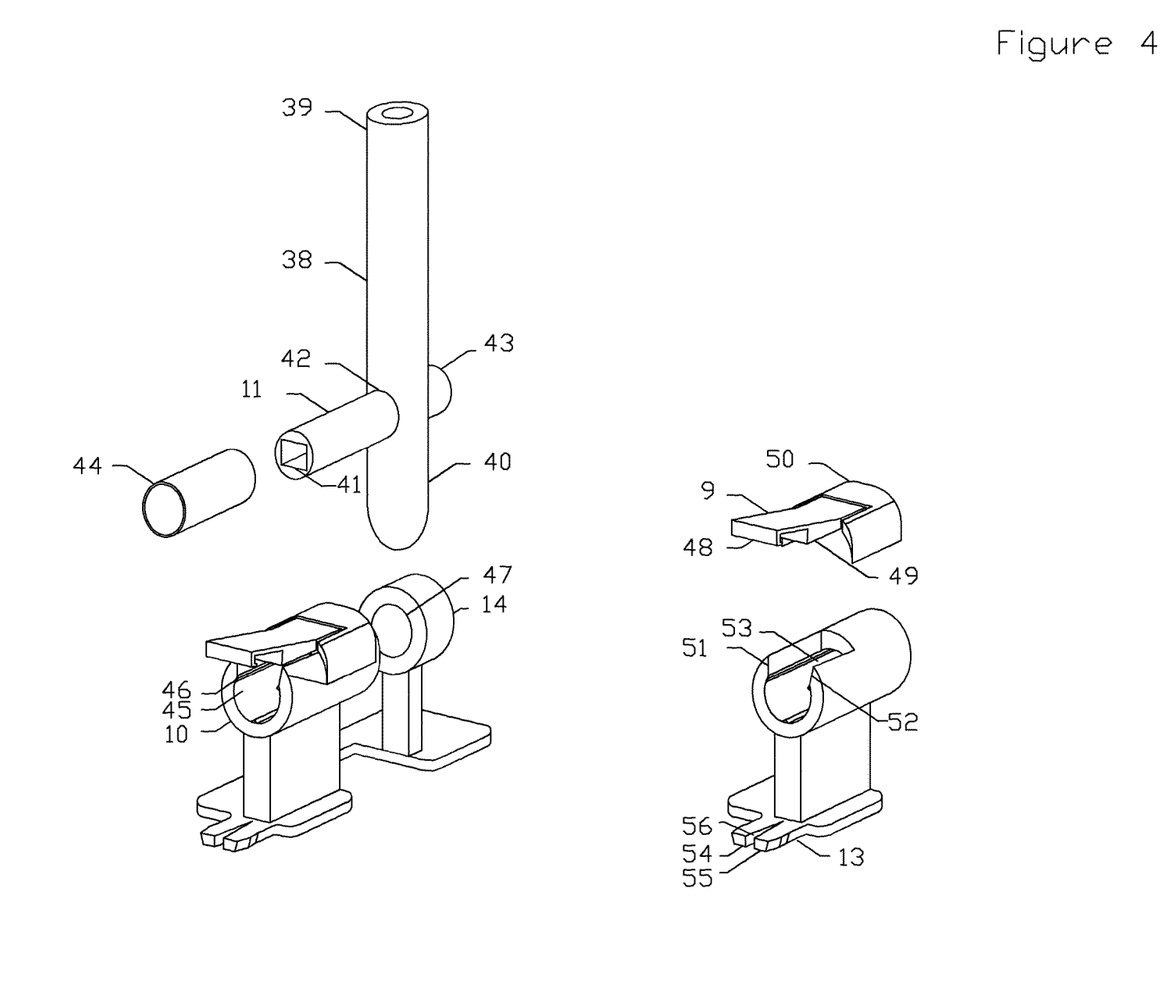
FIG. 4 shows a schematic example of individual components of the positioning guide assembly.

FIG. 4 shows a schematic illustration of an example of individual parts of the positioning guide assembly. The tubular positioning guide 38 has a top portion 39 for entry of an invasive device and a tip 40 through which the invasive device protrudes. The tubular positioning guide 38 is irreversibly attached in a cross configuration to a medial end 42 of the rotation cylinder 11 and to a stabilizer cylinder 43 in a similar manner. The stabilizer cylinder 43 slidably is inserted in an inner tubular space 47 of the stabilizer cylinder holder 14. Inside the rotation cylinder 11, a longitudinal slot 41 is provided to reversibly accommodate the output shaft 28 of FIG. 3A. The rotation cylinder 11 is encased by a thin nonslip tubular elastomer 44 which is located in between of an outer wall of the rotation cylinder 11 and an inner wall 45 of the rotation cylinder holder 10 and which provides friction on both the walls. A plurality of horizontally linear threads 46 are irreversibly attached to the inner wall 45, which is configured to provide firm grasp of the rotation cylinder 11. The rotation cylinder holder 10 has an upper part of a tubular wall cut out to form a horizontal slot 53 bordered by a pair of cut surfaces 51 and 52 of the tubular wall. The lock and release lever 9 is configured as rocker switch which is housed in a dome enclosure 50 fixedly sitting atop the rotation cylinder holder 10 and has a proximal anchor 48 and an insertable block 49. The proximal anchor 48 reversibly is anchorable to the slot 24 of FIG. 3A. Once a proximal part of the lock and release lever 9 is pressed down, the insertable block 49 reversibly engages with the horizontal slot 53 to widen a circumference of the rotation cylinder holder 10. The male piece 13 is configured as dovetailed, having two prongs 54 and 55 separated by a wedge-shaped gap 56 located in the middle of said male piece 13. The prongs 54 and 55 are configured to be horizontally and reversibly squeezed in toward each other to close the gap 56.

Figure 5:
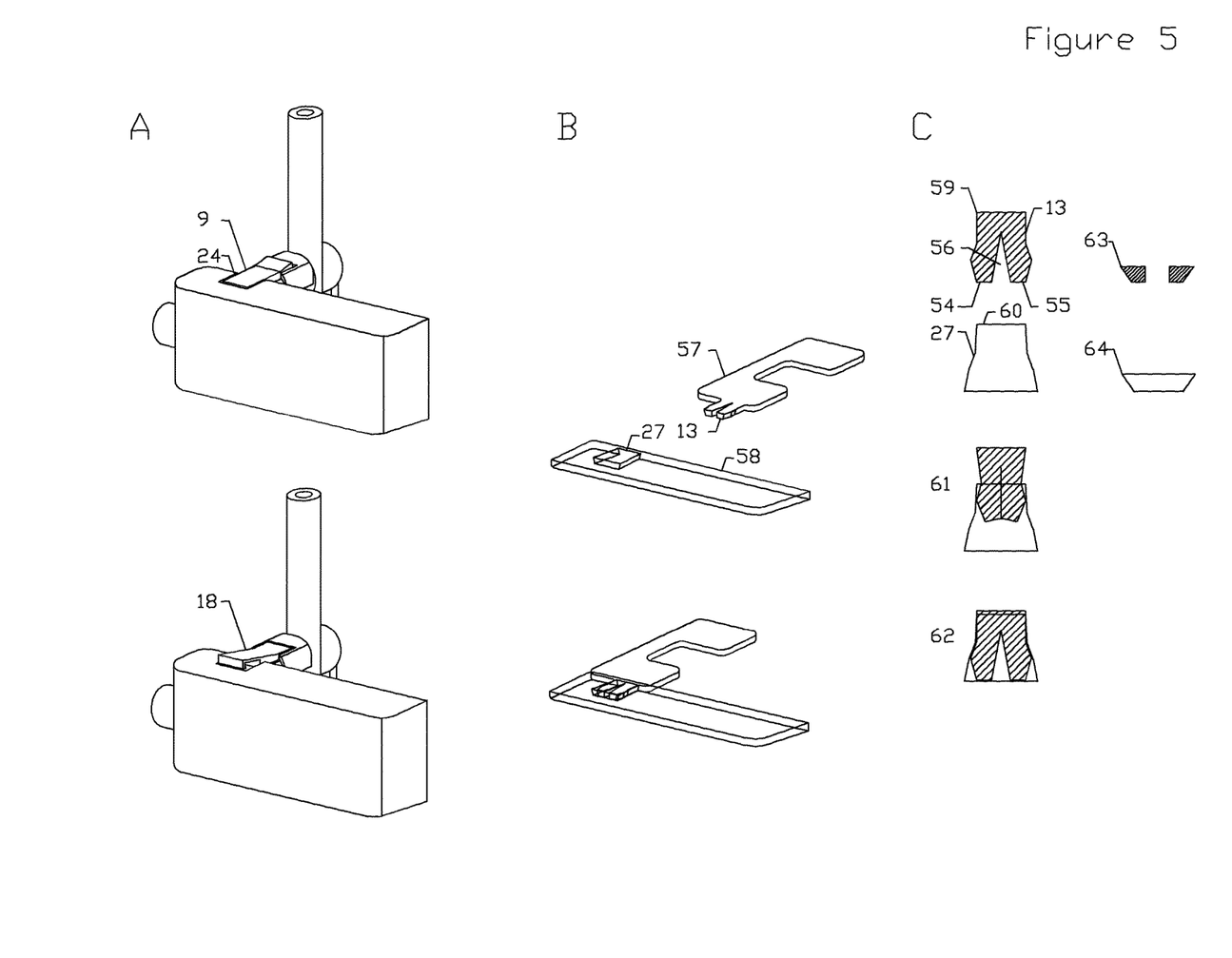
FIG. 5 shows a schematic example of attachment of a positioning guide assembly to a positioning guide control assembly.

FIG. 5 shows a schematic example of connecting a positioning guide assembly to a positioning guide control assembly. Upper drawing of FIG. 5A illustrates the positioning guide assembly securely coupled with the positioning guide control assembly by the lock and release lever 9 of said positioning guide assembly locked in the slot 24 of said positioning guide control assembly. Lower drawing of FIG. 5A shows the positioning guide assembly yet coupled with the positioning guide control assembly while the lock and release lever is disengaged from the slot 24. The lock and release lever 18 represents a disengaged configuration of said lock and release lever 9. In FIG. 5A, drawings of the transducer housing enclosure are removed for a purpose of illustration. FIG. 5B depicts a see-through view of a reversible flat lap joint made by a male piece 13 protruded from a base plate 57 of the positioning guide assembly and a half blind cutout of a female slot 27 of a bottom plate 58 of the positioning guide control assembly. Both plates 57 and 58 are shown with other components of both said assemblies removed for an illustration purpose. FIG. 5C illustrates an example of reversible joint formation by both the male piece and female slot. Upper drawings show an schematic example of a top-down view of a male piece 13 (shaded) and of a female slot 27 on the left and horizontal cross-sectional views 63 and 64, respectively, of two prongs of the male piece (shaded) and the female slot on the right. A base 59 of the male piece 13 is longer than combined length of an advancing side of both the prongs 54 and 55 of said male piece. Both the prongs 54 and 55 are configured to be reversibly squeezed in to close the wedge-shaped gap 56. The advancing side of both the prongs 54 and 55 in an unsqueezed configuration is shorter than an opening 60 of the female slot 27, which allows both the prongs 54 and 55 to slide in without hindrance. Both the male piece and female slot are configured as cross-sectionally isoceles trapezoid, as illustrated in 63 and 64, with an upper side longer than a lower side, which is to prevent downward disengagement of the male piece from the female slot. Mid drawing 61 depicts an ongoing insertion of a male piece into a female slot, showing a collapsed configuration of the prongs of the male piece. Lower drawing 62 shows an expanded male piece fully inserted into and engaged with a female slot, which provides a reversible coupling of the male piece with the female slot.

Figure 6:
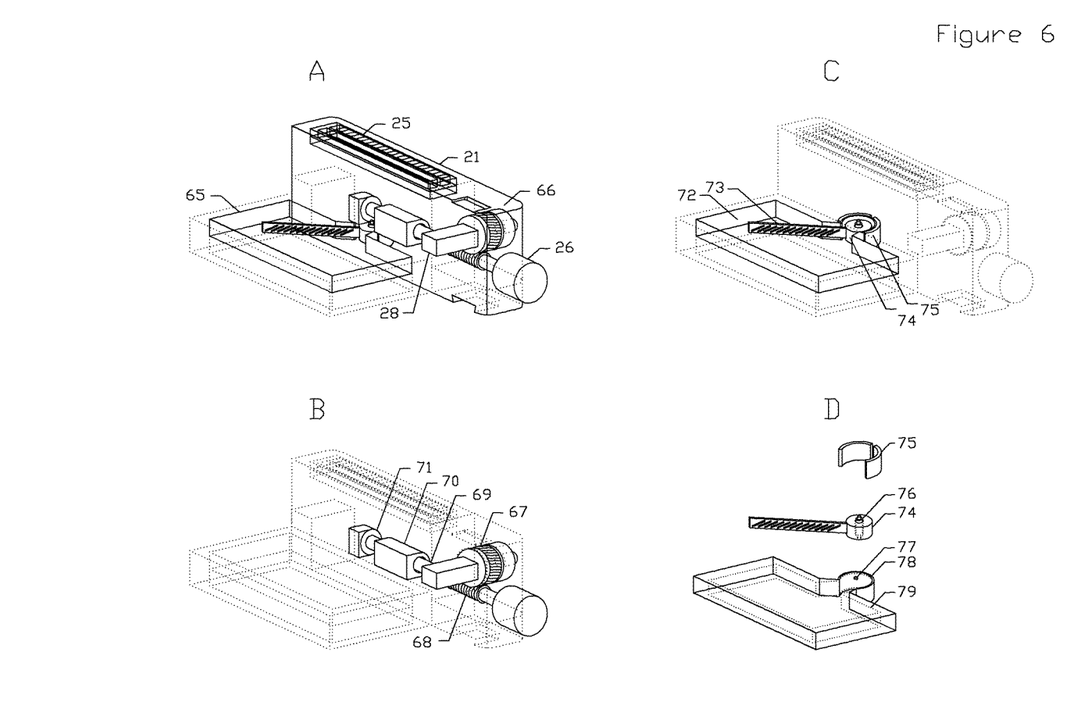
FIG. 6 shows a schematic example of individual components of the positioning guide control assembly.

FIG. 6 shows a schematic illustration of an example of individual components of the positioning guide control assembly. FIG. 6A shows a fully assembled components having the segment digital display 25 of the power and electronic control assembly atop the positioning controller assembly 21, the worm drive arrangement 66 connected to the output shaft 28 and the rotatable knob 26 and the position alignment assembly 65 adjoining at a right angle the positioning controller assembly 21. The transducer housing enclosure is removed in this view for a purpose of illustration. The power and electronic control assembly provides the apparatus with electricity, numerical calculations and data for a range of insertion angles of an invasive tubular device placed in the tubular positioning guide of the positioning guide assembly to reach a tissue target. FIG. 6B shows components of the worm drive arrangement which comprises a worm gear 67 rotatably connected at a right angle to a worm 68, a worm shaft 69, a shaft anchoring portion 70 and a rotary potentiometer 71. The worm shaft 69 is configured to be coaxially connected with a rotary shaft of the rotary potentiometer 71. In FIGS. 6A and B, the rotatable knob 26 rotates the worm 68 which in turn rotates the worm gear 67. Rotation of the worm 68 changes output voltage from the rotary potentiometer 71, which is relayed to the position alignment assembly 65 via the power and electronic control assembly. The power and electronic control assembly electronically coordinates the rotary potentiometer 71 with the position alignment assembly 65. The output shaft 28 transmits rotations of the worm gear 67 to the rotation cylinder 11 of FIG. 2. The shaft anchoring portion 70 is fixedly attached to an inner lateral sidewall of the positioning controller assembly 21 and supports the worm shaft 69.

FIG. 6C shows a galvanometer-type position alignment assembly which comprises a flat rectangular box space 72, an electromagnetic pointing device comprising a linear movable pointer 73 attached to a pivoting wire core 74 and a set of surrounding electromagnetic windings 75. The flat rectangular box is made of substantially ultrasound-transparent polymer(s), and filled with one or a plurality of type(s) of substantially ultrasound-transparent liquid which is electrically non-conductive. The flat rectangular box is leakproof. The linear movable pointer 73 is configured to have a means to reduce drag upon moving inside the liquid. In this particular example, the pointer is fenestrated to reduce an overall lateral surface area of the pointer. FIG. 6D shows one example of a configuration of individual components of an electromagnetic pointing device of the galvanometer-type position alignment assembly, comprising a pivoting wire core 74 with an electrode connection center hub 76 and a pair of electromagnetic windings 75. The pivoting wire core 74 is enclosed by a circular outer housing 78 which adjoins an outer wall 79 of the flat rectangular box. The circular outer housing 78 has an electrode connection hub 77 which comes in contact with the electrode connection center hub 76 of the pivoting wire core 74. The windings 75 are located outside the circular outer housing 78 and encircles tightly said outer housing. Both the pivoting wire core and the windings are electrically connected to the power and electronic control assembly. A range of output voltage generated by the rotary potentiometer, relayed by the power and electronic control assembly, controllably moves the linear movable pointer 73 of the electromagnetic pointing device.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A stereotactic positioning guide apparatus, comprising:
a positioning guide assembly, and a positioning guide control assembly, wherein the positioning guide assembly is configured to be reversibly coupled with and operated by the positioning guide control assembly;
the positioning guide assembly, wherein the positioning guide assembly comprises a tubular positioning guide, a rotation cylinder assembly and a reversible coupling means configured to couple with the positioning guide control assembly, wherein the rotation cylinder assembly comprises a rotation cylinder, wherein the reversible coupling means comprises a lock and release lever and a snap-in male piece, wherein the lock and release lever of the positioning guide assembly is configured to make coupling the lock and release lever with the positioning guide control assembly for operational control of the positioning guide assembly by the positioning guide control assembly synchronize with letting the rotation cylinder be rotatable, wherein the lock and release lever of the positioning guide assembly is configured to make uncoupling the lock and release lever from the positioning guide control assembly synchronize with locking the rotation cylinder so as to guide an invasive tubular device inside the tubular positioning guide slidably passing therethrough, wherein the positioning guide assembly is configured to rotationally adjust and reversibly lock the tubular positioning guide for insertion angle of the invasive tubular device; and
the positioning guide control assembly, wherein the positioning guide control assembly comprises an electromagnetic pointing device, a positioning controller assembly, and an ultrasound transducer enclosure, wherein the positioning controller assembly comprises a manually-drivable worm drive arrangement, wherein the positioning guide control assembly is configured to visually locate a tissue object by the electromagnetic pointing device in a visualized ultrasonographic field to align a longitudinal axis of the tubular positioning guide of the positioning guide assembly with the tissue object in the visualized ultrasonographic field, and wherein the positioning guide control assembly is configured to synchronize locating the tissue object by the electromagnetic pointing device with aligning the longitudinal axis of the tubular positioning guide of the positioning guide assembly with the tissue object by manually rotating the manually-drivable worm drive arrangement.

2. The stereotactic positioning guide apparatus according to claim 1, wherein the positioning guide control assembly further comprises:
a power and electronic control assembly, wherein the power and electronic control assembly is configured to provide the stereotactic positioning guide apparatus with electricity, wherein the power and electronic control assembly is configured to provide numerical calculations and data for a range of insertion angles of the invasive tubular device placed in the tubular positioning guide of the positioning guide assembly to reach the tissue object, and wherein the power and electronic control assembly is configured to electronically coordinate the positioning controller assembly with the electromagnetic pointing device;
the positioning controller assembly, wherein the positioning controller assembly comprises a potentiometer coaxially connected to a worm shaft of the manually-drivable worm drive arrangement, wherein the worm shaft of the manually-drivable worm drive arrangement is configured to be manually rotatable, wherein the potentiometer is configured to electronically measure rotational displacement of the worm shaft, wherein the worm shaft is configured to transmit rotation of the worm shaft through a worm gear of the manually-drivable worm drive arrangement to the rotation cylinder of the positioning guide assembly, and wherein the potentiometer is configured to be electronically connected to the electromagnetic pointing device and to the power and electronic control assembly; and
the electromagnetic pointing device, wherein the electromagnetic pointing device is provided in a galvanometer-type configuration, wherein the electromagnetic pointing device is configured to be located in front of and in parallel with a face of an ultrasound transducer slidably housed in the ultrasound transducer enclosure, wherein the electromagnetic pointing device is configured to be powered and controlled by the power and electronic control assembly, wherein the electromagnetic pointing device is configured to be electronically synchronized with the positioning controller assembly by the power and electronic control assembly, wherein the electromagnetic pointing device comprises a linear movable pointer having one end of the linear movable pointer connected to a pivotable center surrounded by a plurality of electromagnetic windings, wherein the linear movable pointer of the electromagnetic pointing device is configured to produce a linear shadow line in the visualized ultrasonographic field by blocking transmission of a portion of ultrasonographic waves from the ultrasound transducer passing through the electromagnetic pointing device to the tissue object, and wherein the electromagnetic pointing device is configured to synchronize radial movement of the linear movable pointer with rotatably aligning the longitudinal axis of the tubular positioning guide of the positioning guide assembly with the tissue object by manually rotating the worm shaft of the manually-drivable worm drive arrangement of the positioning controller assembly.

3. The positioning guide control assembly according to claim 2, wherein electric output of the potentiometer coaxially connected to the worm shaft by rotation of the worm shaft is configured to be matched with radial movement of the linear movable pointer of the electromagnetic pointing device.

4. The stereotactic positioning guide apparatus according to claim 1, wherein the positioning guide assembly further comprises:
the tubular positioning guide, wherein the tubular positioning guide comprises a tubular conduit configured to fixedly join the rotation cylinder of the rotation cylinder assembly at a right angle, wherein the tubular conduit is configured to slidably pass the invasive tubular device therethrough to reach the tissue object, and wherein the tubular positioning guide is configured to rotate about a joint with the rotation cylinder manually driven by the manually-drivable worm drive arrangement of the positioning guide control assembly;
the rotation cylinder assembly, wherein the rotation cylinder assembly comprises the rotation cylinder, a rotation cylinder holder and a nonslip tubular elastomer, wherein the rotation cylinder is configured to be tightly encircled by the nonslip tubular elastomer, wherein the rotation cylinder is configured to coaxially mate with an output shaft of the manually-drivable worm drive arrangement and to be coaxially rotatable by the output shaft of the manually-drivable worm drive arrangement, wherein the rotation cylinder encircled by the nonslip tubular elastomer is rotatably housed in the rotation cylinder holder, wherein the rotation cylinder holder comprises a cylindrical overtube having an open horizontal slot disposed thereof on the cylindrical overtube, wherein the open horizontal slot is configured to reversibly couple with and uncouple from the lock and release lever of the reversible coupling means, and wherein the nonslip tubular elastomer is configured to provide the rotation cylinder and the rotation cylinder holder with circumferential friction so as to concentrically fasten the rotation cylinder by the rotation cylinder holder;
the lock and release lever, wherein the lock and release lever is configured as pivotable rocker switch, wherein the lock and release lever comprises a proximal anchor and an insertable block connected to the proximal anchor, wherein the proximal anchor is configured to be pivotably inserted in a corresponding slot of the positioning guide control assembly so as to reversibly fasten the positioning guide assembly to the positioning guide control assembly, wherein the insertable block is configured to be pivotably inserted in the open horizontal slot of the cylindrical overtube of the rotation cylinder holder to release the rotation cylinder of the rotation cylinder assembly from the cylindrical overtube so as to let the rotation cylinder be rotatable, wherein the pivotable insertion of the proximal anchor in the corresponding slot of the positioning guide assembly is configured to be synchronized with releasing the rotation cylinder from the cylindrical overtube by the pivotable insertion of the insertable block in the open horizontal slot, wherein the insertable block is configured to be pivotably released from the open horizontal slot of the cylindrical overtube so as to let the cylindrical overtube concentrically lock the rotation cylinder of the rotation cylinder assembly, and wherein the concentric locking of the rotation cylinder by the cylindrical overtube by the pivotable release of the insertable block from the open horizontal slot of the cylindrical overtube is configured to be synchronized with pivotable release of the proximal anchor from the corresponding slot of the positioning guide control assembly; and
the snap-in male piece, wherein the snap-in male piece is provided as a flat projection from a bottom wall of the positioning guide assembly, wherein the snap-in male piece is configured to mate with a female slot disposed on a bottom wall of the positioning guide controller assembly, wherein the snap-in male piece is configured to reversibly couple with the female slot so as to reversibly fasten the positioning guide assembly to the positioning guide control assembly.

5. A method of aligning a tubular positioning guide of a positioning guide assembly of a stereotactic positioning guide apparatus with a tissue object, comprising:
providing a stereotactic positioning guide apparatus comprising a positioning guide assembly and a positioning guide control assembly;
placing in a head of an ultrasound transducer in an ultrasound transducer enclosure of the positioning guide control assembly;
snapping a snap-in male piece of the positioning guide assembly in a female slot of the positioning guide control assembly so as to couple the positioning guide assembly with the positioning guide control assembly, and slidably engaging an output shaft of a manually-drivable worm drive arrangement of the positioning guide control assembly with a rotation cylinder of the positioning guide assembly;
fastenably inserting a proximal anchor of a lock and release lever of the positioning guide assembly in a corresponding slot of the positioning guide control assembly, wherein an insertable block of the lock and release lever is synchronizably inserted in an open horizontal slot of a cylindrical overtube of the positioning guide assembly with the insertion of the proximal anchor of the lock and release lever of the positioning guide assembly in the corresponding slot of the positioning guide control assembly, wherein the insertion of the insertable block of the lock and release lever into the open horizontal slot of the cylindrical overtube of the positioning guide assembly is synchronized to loosen the rotation cylinder connected to a tubular positioning guide of the positioning guide assembly from the cylindrical overtube so as to let the tubular positioning guide of the positioning guide assembly be rotatable;

powering up the positioning guide control assembly;

placing a proximal end of the stereotactic positioning guide apparatus on a skin overlying a tissue object, wherein a bottom wall of the positioning guide assembly contacts the skin;

ultrasonographically visualizing an area of the tissue object and the tissue object in an visualized ultrasonographic field of a main ultrasonographic machine;

manually rotating a worm shaft of the manually-drivable worm drive arrangement of the positioning guide control assembly;

electronically measuring manual rotation of the worm shaft of the manually-drivable worm drive arrangement by a potentiometer coaxially attached to the worm shaft of the manually-drivable worm drive arrangement;

providing a power and electronic control assembly with an electronic information of the manual rotation of the worm shaft of the manually-drivable worm drive arrangement;

providing an electromagnetic pointing device of the positioning guide control assembly with an electricity from the power and electronic control assembly based on the electronic information of the manual rotation of the worm shaft of the manually-drivable worm drive arrangement so as to controllably and radially move a linear movable pointer of the electromagnetic pointing device;

synchronizing the manual rotation of the worm shaft of the manually-drivable worm drive arrangement with the radial movement of the linear movable pointer of the electromagnetic pointing device by the power and electronic control means;

continuing to manually rotate the worm shaft of the manually-drivable worm drive arrangement until a linear shadow line in the visual ultrasonographic field produced by the linear movable pointer of the electromagnetic pointing device intersects the tissue object in the visualized ultrasonographic field, wherein the tubular positioning guide is synchronizably rotated about the rotation cylinder of the positioning guide assembly until a longitudinal axis of the tubular axis is aligned with the tissue object, and wherein the intersection of the tissue object by the linear shadow line is coincided with the aligning of the longitudinal axis of the tubular positioning guide with the tissue object; and releasing the proximal anchor of the lock and release lever of the positioning guide assembly from the corresponding slot of the positioning guide control assembly, wherein the insertable block of the lock and release lever is synchronizably released from the open horizontal slot of the cylindrical overtube of the positioning guide assembly with the release of the proximal anchor of the lock and release lever of the positioning guide assembly from the corresponding slot of the positioning guide control assembly, wherein the release of the insertable block of the lock and release lever from the open horizontal slot of the cylindrical overtube of the positioning guide assembly is synchronized to concentrically lock the rotation cylinder connected to a tubular positioning guide of the positioning guide assembly by the cylindrical overtube.

* * * * *